(12) United States Patent
Wakabayashi et al.

(10) Patent No.: US 7,927,604 B2
(45) Date of Patent: Apr. 19, 2011

(54) METHOD OF PREPARING A SEAWEED DEGRADATION PRODUCT AND A COMPOSITION FOR PREPARING A SEAWEED DEGRADATION PRODUCT

(75) Inventors: Masayuki Wakabayashi, Nanao (JP); Tetsuya Nakamura, Nanao (JP); Minoru Noda, Moriya (JP); Fumio Noda, Nanao (KP)

(73) Assignee: Sugiyo Co., Ltd., Ishikawa (JP)

( * ) Notice: Subject to any disclaimer, the term of this patent is extended or adjusted under 35 U.S.C. 154(b) by 490 days.

(21) Appl. No.: 11/959,500

(22) Filed: Dec. 19, 2007

(65) Prior Publication Data

US 2008/0175858 A1 Jul. 24, 2008

(30) Foreign Application Priority Data

Dec. 25, 2006 (JP) ................. 2006-348518

(51) Int. Cl.
*A61K 36/00* (2006.01)
*A61K 36/02* (2006.01)
*C12P 1/04* (2006.01)
*C12N 1/20* (2006.01)
*C12N 9/00* (2006.01)
*A23L 1/28* (2006.01)
*A23L 1/05* (2006.01)

(52) U.S. Cl. ............ 424/195.17; 424/725; 435/170; 435/252.3; 435/183; 426/655; 426/575

(58) Field of Classification Search ............ None
See application file for complete search history.

(56) References Cited

U.S. PATENT DOCUMENTS 5,801,050 A 9/1998 Uchida et al.
2006/0128946 A1 * 6/2006 Weiner et al. ................ 530/370

FOREIGN PATENT DOCUMENTS

| JP | 58149666 A | * | 9/1983 |
| JP | 08-298937 | | 11/1996 |
| JP | 2005198518 A | * | 7/2005 |

OTHER PUBLICATIONS

Curtis et al, Estimating prokaryotic diversity and its limits, Proceedings of the National Academy of Sciences of the United States of America 99 (16): 10494-9, 2002.*
Schloss et al, Status of the microbial census, Microbiology and Molecular Biology Reviews 68 (4): 686-91, 2004.*
Descamps et al, Isolation and culture of a marine bacterium degrading the sulfated fucans from marine brown algae, Marine Biotechnology (2006), 8(1), 27-39.*
Sakai et al, A marine strain of Flavobacteriaceae utilizes brown seaweed fucoidan, Marine Biotechnology (2002), 4(4), 399-405.*
Ohta et al, Enzymatic properties and nucleotide and amino acid sequences of a thermostable beta-agarase from a novel species of deep-sea Microbulbifer, Applied microbiology and biotechnology, (May 2004) vol. 64, No. 4, pp. 505-514.*

* cited by examiner

*Primary Examiner* — Qiuwen Mi
(74) *Attorney, Agent, or Firm* — Renner, Otto, Boisselle & Sklar, LLP

(57) ABSTRACT

A method to prepare seaweed degradation product comprising contacting a bacterium having 16S rRNA sequence consisting of the nucleic acid sequence as recited in SEQ ID NO: 1 with a seaweed is provided.

6 Claims, 11 Drawing Sheets

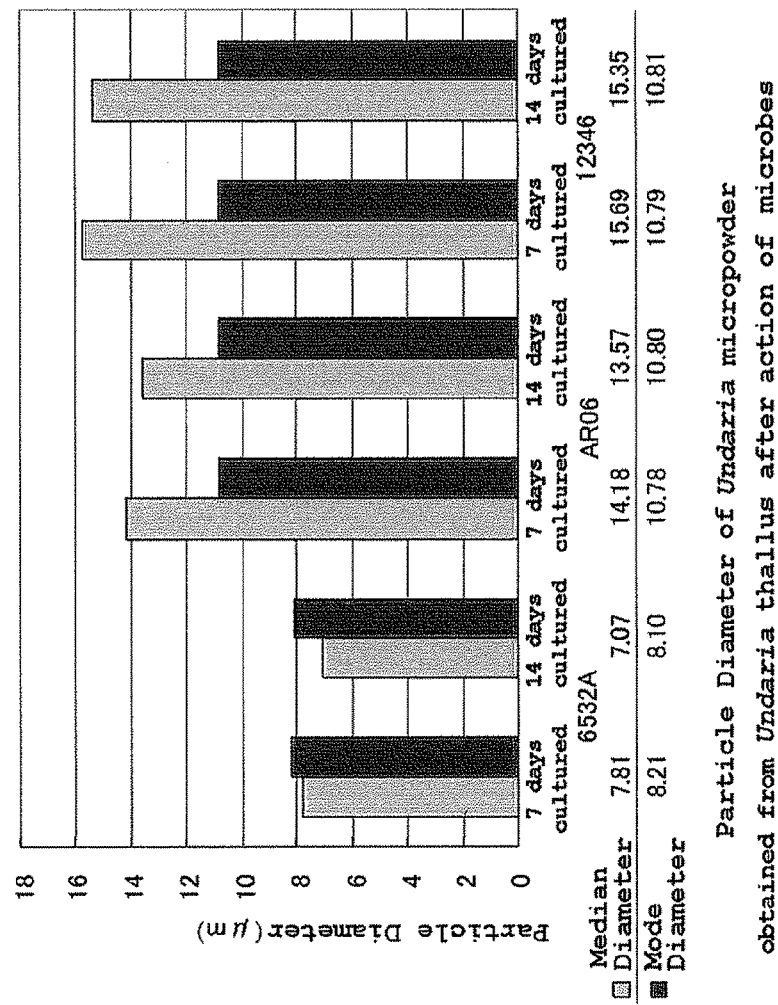

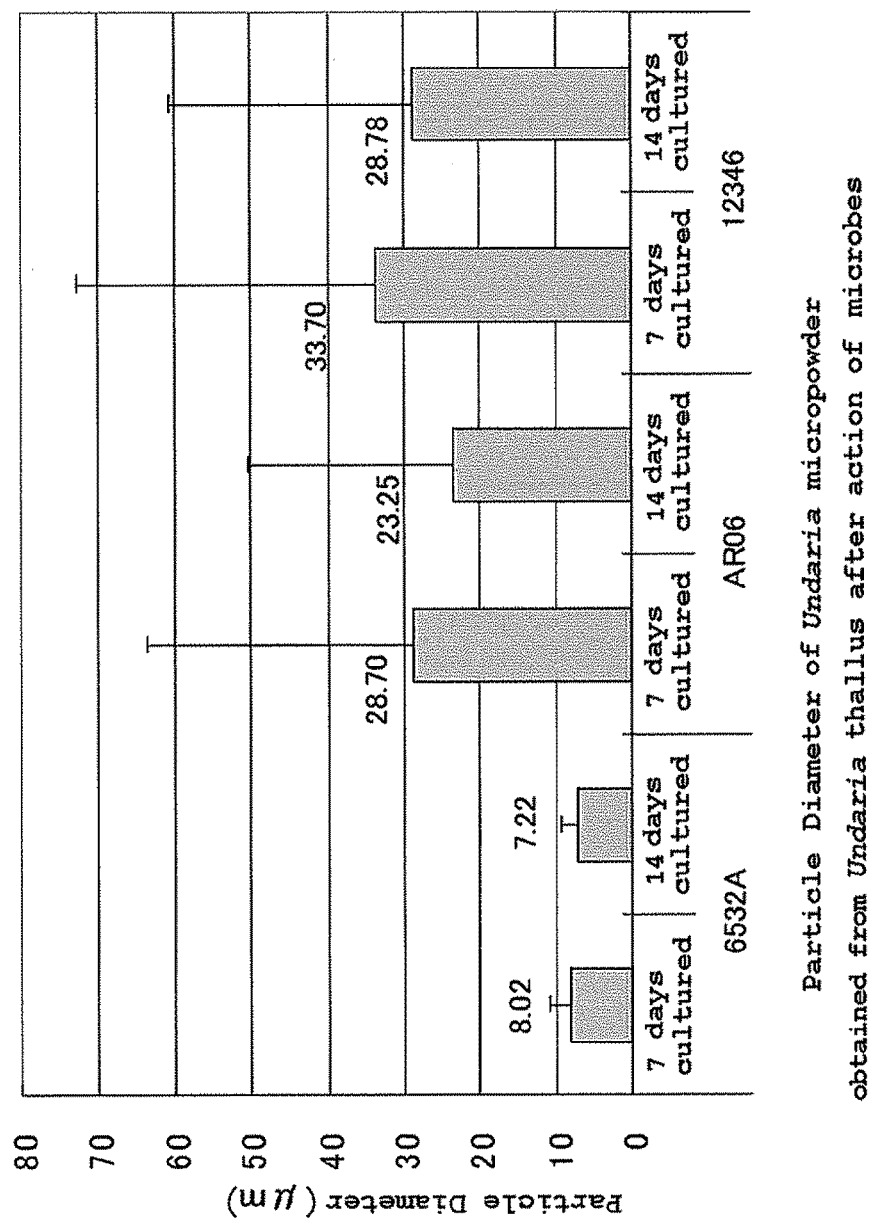

SEQUENCE LISTING

```
<160> NUMBER OF SEQ ID NOS: 1

<210> SEQ ID NO 1
<211> LENGTH: 476
<212> TYPE: RNA
<213> ORGANISM: Microbulbifer hydrolyticus
<220> FEATURE:
<221> NAME/KEY: misc_feature
<222> LOCATION: (416)..(416)
<223> OTHER INFORMATION: n is a, c, g, or u
```

-continued

```
<400> SEQUENCE: 1
aacgcuggcg gcaggccuaa cacaugcaag ucgagcgcga acgguccuuc gggacuuauu       60
agagcggcgg acgggugagu aaugcauagg aaucugccca guaguggggg auagcccggg      120
gaaacccgga uuaauaccgc auacguccua cgggagaaag caggggaucu ucggaccuug      180
cgcuauugga ugagccuaug ucggauuagc uuguuggugg gguaacggcc caccaaggcg      240
acgauccgua gcuggucuga gaggaugauc agccacacug ggacugagac acggcccaga      300
cuccuacggg aggcagcagu ggggaauauu gcacaauggg ggaaacccug augcagccau      360
gccgcgugug ugaagaaggc cuucggguug uaaagcacuu ucaguaggga ggaagnccu       420 aaaguuaaua ccuuuaggga uugacguuac cuacagaaga agcaccggcu aacucc          476
```

METHOD OF PREPARING A SEAWEED DEGRADATION PRODUCT AND A COMPOSITION FOR PREPARING A SEAWEED DEGRADATION PRODUCT

TECHNICAL FIELD

The present invention relates to a method of preparing a seaweed degradation product using a bacteria and a composition for preparing a seaweed degradation product using a bacteria. Furthermore, the present invention relates to a composition and an additive for food and beverage products containing a seaweed degradation product.

BACKGROUND ART

When seaweed powder is produced, it was common to obtain the powder by physical treatment. Powder prepared by these physical treatments is obtained by powdering seaweed in a dried state. Thus, the particle diameter of the resultant seaweed powder is heterogeneous. Furthermore, when the resultant seaweed powder is utilized in food, the particles of the seaweed powder swell by water absorption, and the particle diameter and size of the powder becomes even less heterogeneous. For these reasons, it was difficult to obtain a seaweed powder having good suspension and floating properties by powdering seaweed with physical treatments.

In the natural world, microbes such as bacteria adhere to the seaweed thallus surface. There is a microbe having an ability to make a hole through a seaweed thallus tissue or to degrade thallus tissue. Therefore, as a seaweed degradation technique other than the physical treatments, a method using a microbe such as a bacterium of *Alteromonas* genus is known (patent document 1). However this method has a disadvantage, as it is required to prepare seaweed degradation products by physical pre-treatment of seaweeds into debris prior to using a bacterium of genus *Alteromonas*. Furthermore, although the seaweed degradation product prepared by a bacterium of genus *Alteromonas* can be used as a feed for fry, Crustaceans and the molluscous larva, this seaweed degradation product is not sufficiently degraded and appears poor in suspension. Therefore, there is a problem that this seaweed degradation product is not suitable for a composition and/or supplement for food and beverage products.

[Patent document 1] Japanese patent No. 2772772 specification

DISCLOSURE OF THE INVENTION

Problems to be Solved by the Invention

In view of the aforementioned circumstances, it is a problem to be solved by the present invention to obtain a seaweed degradation product having a good suspension property, which can be used in food and beverages.

Means for Solving the Problems

The present inventors isolated from an environment having many marine bacteria with the ability to degrade seaweed thallus tissues and conducted studies on these bacteria. As a result, the present inventors found among these bacteria a microbe strain which strongly degrades seaweed thallus tissues. By utilizing this strain, an intercellular substance of the seaweed was degraded, separating individual cells, and thus allowing one to obtain seaweed particles in a single-cell state.

The aforementioned problem was solved by using the bacterium for a preparation of a seaweed degradation product.

Thus, according to the present invention, the following is provided:

(Item 1)

A method to prepare a seaweed degradation product comprising contacting a bacterium belonging to genus *Microbulbifer* with a seaweed.

(Item 2)

A method to prepare seaweed degradation product comprising contacting a bacterium and seaweed, wherein said bacterium has the following mycological properties:

Morphological Properties:
Shape of the cell: Rod
Size of the cell: About 1.0 μm (width)×about 3.2 μm (length)
Presence or absence of motility: Presence
Presence or absence of spore: Absence;
Culture Properties:
In Marine Agar 2216
Producing no pigment, forming a recess in the center of a colony and the colony has a wavy circumference;
Liquefying an agar plate medium;
In Marine Broth 2216
Proliferating well and forming a floc when cultured at 30° C. for 48 hours;
Physiologic Properties:
Gram stain: Gram negative
Pigmentation: Not produced
Oxidase: Positive
Catalase: Positive
Range of growth: No growth at 4° C., good growth at 30° C., and growth is possible at 50° C.
Behavior toward oxygen: Aerobic
O-F test: O-type (according to an MOF medium which is a Hughloifson medium developed for marine bacteria)
Requirement of NaCl: No growth with 0-1% NaCl, growth at 2.5-5.0%, NaCl is required for growth;
Polysaccharide Decomposition Activity of the Extracellular Enzymes:
Alginic acid: Positive
Fucoidan: Negative
Laminarin: Negative
Agar: Positive (strongly: liquefying an agar plate medium in an agar plate).

(Item 3)

A method to prepare a seaweed degradation product comprising contacting seaweeds with a bacterium having a 16S rRNA sequence consisting of the nucleic acid sequence as recited in SEQ ID NO: 1.

(Item 4)

The method according to any one of Items 1-3 wherein said bacterium is *Microbulbifer* sp. strain 6532A (accession number FERM P-21069).

(Item 5)

The method according to any one of Items 1-3 wherein said seaweed is a brown algae.

(Item 6)

The method according to any one of Items 1-3 wherein said seaweed is *Undaria*, kelp or *Ecklonia cava*.

(Item 7)

A composition for preparing a seaweed degradation product comprising a bacterium belonging to genus *Microbulbifer*.

(Item 8)
A composition for preparing a seaweed degradation product comprising a bacterium, wherein said bacterium has the following mycological properties:
Morphological Properties:
Shape of the cell: Rod
Size of the cell: About 1.0 μm (width)×about 3.2 μm (length)
Presence or absence of motility: Presence
Presence or absence of spore: Absence;
Culture Properties:
In Marine Agar 2216
Producing no pigment, forming a recess in the center of a colony and the colony has a wavy circumference;
Liquefying an agar plate medium;
In Marine Broth 2216
Proliferating well and forming a floc when cultured at 30° C. for 48 hours;
Physiologic Properties:
Gram stain: Gram negative
Pigmentation: Not produced
Oxidase: Positive
Catalase: Positive
Range of growth: No growth at 4° C., good growth at 30° C., and growth is possible at 50° C.
Behavior toward oxygen: Aerobic
O-F test: O-type (according to an MOF medium which is a Hughloifson medium developed for marine bacteria)
Requirement of NaCl: No growth with 0-1% NaCl, growth at 2.5-5.0%, NaCl is required for growth;
Polysaccharide Decomposition Activity of the Extracellular Enzymes:
Alginic acid: Positive
Fucoidan: Negative
Laminarin: Negative
Agar: Positive (strongly: liquefying an agar plate medium in an agar plate).

(Item 9)
A composition for preparing a seaweed degradation product comprising a bacterium, wherein said bacterium has a 16S rRNA sequence consisting of the nucleic acid sequence as recited in SEQ ID NO: 1.

(Item 10)
The composition according to any one of items 7-9 wherein said bacterium is *Microbulbifer* sp. strain 6532A (accession number FERM P-21069).

(Item 11)
A composition according to any one of items 7-9 wherein said seaweed is a brown algae.

(Item 12)
A composition according to any one of items 7-9 said seaweed is *Undaria*, kelp or *Ecklonia cava*.

(Item 13)
A composition for food and beverage products containing the seaweed degradation product prepared by the method according to any one of Items 1-3.

(Item 14)
A composition for food and beverage products containing the seaweed degradation product prepared by the method according to any one of Items 1-3, wherein said composition is used for the preparation of a food and beverage product selected from the group consisting of a drink, powder for drink preparation, a supplement, soup, seasoning, butter, jam, margarine, dressing, mayonnaise, fish sausage, a delicacy and confectionary.

(Item 15)
An external preparation for skin containing the seaweed degradation product prepared by the method according to any one of Items 1-3.

(Item 16)
The external preparation for skin according to Item 15, which is selected from the group consisting of a cosmetic preparation, humectant, face lotion, cream, gel, ointment, emulsion, cosmetic nutrient lotion, mask, face wash preparation, cleansing agent, hair care preparation, soap, bath agent, shampoo, conditioner, lipstick, rouge and foundation.

(Item 17)
An additive for food and beverage products containing the seaweed degradation product prepared by the method according to any one of Items 1-3.

(Item 18)
A crude enzyme solution prepared from a bacterium, wherein said bacterium has the following mycological properties:
Morphological Properties:
Shape of the cell: Rod
Size of the cell: About 1.0 μm (width)×about 3.2 μm (length)
Presence or absence of motility: Presence
Presence or absence of spore: Absence;
Culture Properties:
In Marine Agar 2216
Producing no pigment, forming a recess in the center of a colony and the colony has a wavy circumference;
Liquefying an agar plate medium;
In Marine Broth 2216
Proliferating well and forming a floc when cultured at 30° C. for 48 hours;
Physiologic Properties:
Gram stain: Gram negative
Pigmentation: Not produced
Oxidase: Positive
Catalase: Positive
Range of growth: No growth at 4° C., good growth at 30° C., and growth is possible at 50° C.
Behavior toward oxygen: Aerobic
O-F test: O-type (according to an MOF medium which is a Hughloifson medium developed for marine bacteria)
Requirement of NaCl: No growth with 0-1% NaCl, growth at 2.5-5.0%, NaCl is required for growth;
Polysaccharide Decomposition Activity of the Extra cellular Enzymes:
Alginic acid: Positive
Fucoidan: Negative
Laminarin: Negative
Agar: Positive (strongly: liquefying an agar plate medium in an agar plate).

(Item 19)
A method to prepare a seaweed degradation product comprising contacting seaweeds with the crude enzyme solution according to Item 18.

(Item 20)
The method according to Item 19 wherein said seaweed is a brown algae.

(Item 21)
The method according to Item 19 wherein said seaweed is *Undaria*, kelp or *Ecklonia cava*.

(Item 22)
A composition for preparing a seaweed degradation product comprising the crude enzyme solution according to Item 18.

(Item 23)

The composition according to Item 22 wherein said seaweed is a brown algae.

(Item 24)

The composition according to Item 22 wherein said seaweed is *Undaria*, kelp or *Ecklonia cava*.

EFFECTS OF THE INVENTION

According to the present invention, a microbe of the present invention is acted on seaweed thallus, then seaweed particles which are in a single-cell state can be obtained. The seaweed particles thus obtained have good suspension, floating and diffusion properties, and is useful for various forms of foods and drinks.

BRIEF DESCRIPTION OF THE DRAWINGS

FIG. 10 shows the particle diameter (median diameter and mode diameter, unit in μm) of *Undaria* micro powder obtained after *Undaria* thallus (about 10 mm square) was treated by the microbe for seven days or 14 days. The particle diameter distributions of *Undaria* micro powder after a microbe strain 6532A, strain AR06 or strain 12346 was inoculated into a medium containing *Undaria pinnatifida* thallus and cultured for seven or 14 days are shown.

FIG. 11 shows the average particle diameter of *Undaria* micro powder obtained after *Undaria* thallus was treated for seven days or 14 days. The average particle diameter of *Undaria pinnatifida* micro powder after a microbe strain 6532A, strain AR06 or strain 12346 was inoculated into a medium containing *Undaria* thallus and cultured for seven or 14 days are shown.

SEQUENCE LISTING FREE TEXT

Figure 1:
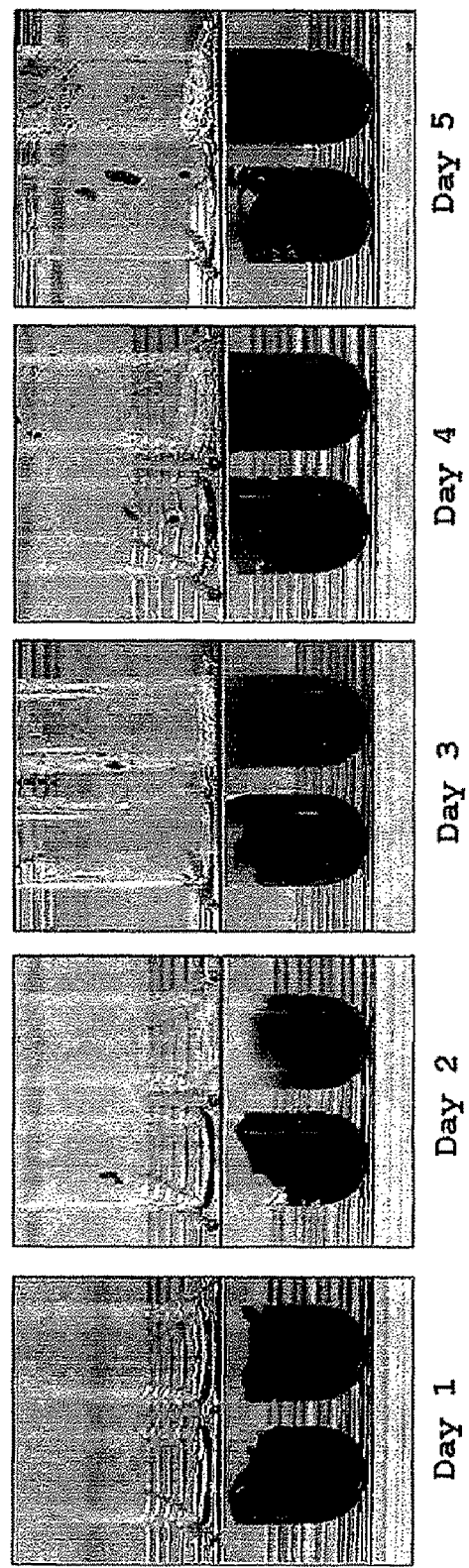
FIG. 1 shows a time course change of particle formation of *Undaria* thallus by the action of a microbe.

SEQ ID NO: 1: a 16S rRNA sequence of *Microbulbifer* sp. 6532A strain (accession number FERM P-21069).

BEST MODE FOR CARRYING OUT THE INVENTION

The present invention is explained as follows. Throughout the present specification, it should be understood that, unless otherwise specified, the expression in the singular form should include the concept of the plural form. Furthermore, it should be understood that, unless otherwise specified, terms used in the present specification is used in the meanings that is usually used in the art. Thus, unless otherwise specified, all technical and scientific terms used in the present specification have a meaning that is the same as what is commonly understood by those skilled in the art of the art to which the invention belongs. In the case of contradiction, the present specification (including definitions) dominates.

One of the features of the bacteria strain used in the present invention is that it acts on structural polysaccharides which maintain the cellular structure of a brown algae, especially *Undaria* and those of Laminariaceae family, and thus degrade these seaweeds down to single cells. In order to search for marine bacteria having the ability to degrade seaweeds, the present inventors obtained 124 seaweed samples used as isolation sources at 28 spots of the Japanese coast. Four hundreds or more marine bacteria were isolated from these isolation sources, and from these strains, 64 strains that seemed to have an ability of seaweed degradation were isolated. Furthermore, the present inventors conducted various tests regarding seaweed degradation ability, ability to degrade various polysaccharides, bacteriological properties and the like. As a result, the present inventors succeeded in obtaining a marine bacterial strain is particularly useful.

As used herein the term "seaweed" refers to an algae from ocean which has a visible size.

A bacterium used in the present invention is preferably a bacterium belonging to the genus *Microbulbifer*.

A bacterium used in the present invention preferably has morphological properties as follows:

Shape of the cell: Rod

Size of the cell: About 1.0 μm (width)×about 3.2 μm (length)

Presence or absence of motility: Presence

Presence or absence of spore: Absence.

A bacterium used in the present invention preferably has culture properties that the bacterium does not produce a pigment in Marine Agar 2216, but forms a recess in the center of a colony and the colony has a wavy circumference.

A bacterium used in the present invention preferably has a culture property which liquefies an agar plate medium.

A bacterium used in the present invention preferably has culture properties that in Marine Broth 2216, it proliferates well and forms a floc when cultured at 30° C. for 48 hours.

A bacterium used in the present invention preferably has the following physiological properties:
Gram stain: Gram negative
Pigmentation: Not produced
Oxidase: Positive
Catalase: Positive
Range of growth: No growth at 4° C., good growth at 30° C., and growth is possible at 50° C.
Behavior toward oxygen: Aerobic
O-F test: O-type (according to an MOF medium which is a Hughloifson medium developed for marine bacteria)
Requirement of NaCl: No growth with 0-1% NaCl, growth at 2.5-5.0%, and thus NaCl is required for growth.

A bacterium used in the present invention preferably has following polysaccharide decomposition activity of the extracellular enzymes:
Alginic acid: Positive
Fucoidan: Negative
Laminarin: Negative
Agar: Positive (strongly: liquefying an agar plate medium in an agar plate).

A bacterium used in the present invention is preferably a bacterium having a 16S rRNA sequence which hybridizes to the nucleic acid sequence recited in SEQ ID NO: 1 under a stringent condition. Furthermore, a bacterium used in the present invention is preferably a bacterium having a 16S rRNA sequence consisting of a sequence with one or several deletions additions or substitutions to the nucleic acid sequence recited in SEQ ID NO: 1. A bacterium used in the present invention is more preferably a bacterium having a 16S rRNA sequence consisting of the nucleic acid sequence recited in SEQ ID NO: 1. Furthermore, a bacterium used in the present invention is most preferably *Microbulbifer* sp. strain 6532A (accession number FERM P-21069).

A seaweed degraded in the present invention is preferably a brown algae, and more preferably *Undaria*, kelp (for example, *Laminaria japonica*, a brown algae of Laminariaceae family) or *Ecklonia cava*.

In order to obtain a seaweed degradation product according to the present invention, one can directly culture the bacteria of the present invention with seaweeds, or add a crude or purified enzyme solution prepared from the bacteria of the present invention to seaweeds.

The seaweed degradation product produced by the method of the present invention can be used as a composition for food and beverage products, as well as an agent and additive for external preparation for skin. Food and beverage products containing the seaweed degradation product of the present invention can be any food and beverage product. The food and beverage product can be a solid, semisolid or liquid, but it is preferably a liquid. The food and beverage product is preferably a health food, and more preferably a health drink, but is not limited to these. The health food can be used for the same usual application as the seaweed degradation product included in the health food. Examples of food and beverage products containing the seaweed degradation product of the present invention include, but not limited to: for example, (1) drinks (e.g., liquid (seaweed sports drink and the like), powder (seaweed and green vegetable juice and the like), supplement (containing a-lipoic acid, lycopene, BRM in addition to the seaweed degradation product of the present invention), local souvenir (containing deep-ocean water, Hakusan underflow water and the like in addition to the seaweed degradation product of the present invention)); (2) soup (such as seaweed soup and the like); (3) seasoning (seasoning for bread (seaweed jam, seaweed margarine and the like), seasoning for salad, dressing, mayonnaise and the like); (4) solid food (kamaboko (fish sausage), hors d'oeuvres, Date-maki (rolled sweet egg and fish cake), delicacy (as a secondary raw material) and the like); (5) soluble seaweed powder (bulk materials (confectionary material and the like)) and the like.

Even more particularly, for example, food and beverage products containing the seaweed degradation product of the present invention can be ice confectionary (for example, ice cream, ice milk, sorbet and the like), luxury drinks (for example, refreshing drinks, carbonated drinks (such as soda, lemonade), spiced drinks, alcoholic drinks, powdered juice and the like), dairy products (milk, yogurt, ice cream, butter, margarine, cheese, whipped cream and the like), confectionery (Western-style confectionery, Japanese-style confectionery, snacks and the like, for example, bean jam, sweetened and jellied bean paste, steamed bun, chocolate, gum, jelly, agar, almond jelly, cake, castella, cookie, rice cracker, tablet and the like), bread, rice cake, fish paste product (kamaboko, a tubular fish paste product and the like), processed animal meat product (sausage, ham and the like), processed fruit product (jam, marmalade, fruit sauce and the like), seasoning (dressing, mayonnaise, miso and the like), noodles (udon, buckwheat noodle and the like), pickles, animal meat, fish meat, bottled fruit, and canned food.

No special step is needed in order to add the seaweed degradation product prepared by the method of the present invention to a food and beverage product. The seaweed degradation product prepared by the method of the present invention can be added with raw materials at the initial step of a manufacturing process for a food and beverage product, or during the manufacturing process, or at a later step during the manufacturing process. According to the type and the state of the food and beverage product, a method for addition is selected from conventional methods including mixing, kneading, dissolving, dipping, sprinkling, spraying, spreading and the like. The food and beverage product of the present invention can be prepared according to a method known to those skilled in the art.

The seaweed degradation product of the present invention can be used for an external preparation for skin. There is no particular limitation regarding the form of the external preparation for skin. For example, the external preparation for skin can be used in a form of liquid, gel, cream, granule, solid or the like. When the seaweed degradation product of the present invention is used as an external preparation for skin, it can be formulated in cosmetics, quasi-drugs, drugs and the like such as cosmetic preparation, humectant, face lotion, cream, gel, ointment, emulsion, cosmetic nutrient lotion, mask, face wash preparations cleansing agent, hair care preparation, soap, bath agent, shampoo, conditioner, lipstick, rouge, foundation and the like.

EXAMPLES

Isolation of *Microbulbifer* sp. Strain 6532A

124 Samples of seaweeds washed ashore were collected from 28 places along the coasts of the Japan Sea. These samples were used as isolation sources to screen for a marine bacterium.

The seaweed which drifted at the coasts of Ishikawa and Toyama prefectures were collected as isolation sources. 0.1% Ammonium nitrate, 0.002% dipotassium phosphate, and 0.05% yeast extract were added to an artificial seawater to make an artificial seawater medium. This medium was sterilized in autoclave. Furthermore, a medium containing 1.5% agar was added to the artificial seawater medium and used as a plate medium.

10% weight of the collected seaweeds were added to the artificial seawater medium (NaCl 30.0 g, KCl 0.7 g, $MgCl_2 \cdot 6H_2O$ 10.8 g, $MgSO_4 \cdot 7H_2O$ 5.4 g, $CaCl_2 \cdot 2H_2O$ 1.0 g, $NH_4NO_3$ 1.0 g, $K_2HPO_4$ 0.02 g, Yeast Extract 0.5 g; distilled water 1,000 ml), and then cultured for 2-5 days at 30° C. with stirring. After stirring the culture, a plate medium prepared by adding 1% *Undaria* powder (Riken Vitamin Co., Ltd., Tokyo, WAKAMIDORI) to the aforementioned artificial seawater medium was applied to the cultured solution, and incubated to form colonies. By this culturing, 111 strains of microbes that seemed to have seaweed assimilating ability were isolated. Furthermore, colonies were picked based on the characteristics of formation with or without transparent rings on the surface of the culture, medium dissolution and the like, and 64 strains were isolated as seaweed degrading bacteria. Furthermore, the purified and cultured colonies of each strain were inoculated to a artificial seawater medium added with 1% seaweed thallus (about 9.0-15.0 mm square) and tested for seaweed degradation ability. These were cultured at 30° C. with stirring, and a microbe which showed the degradation and particles formation from seaweed thallus was selected.

Then, based on the bacteriological properties and the 16S rRNA sequence of the marine bacterium obtained by the aforementioned screening, species of this bacterium was identified. The homogeny search of the 16S rRNA sequence and the analysis of the taxonomic position was performed based on BLAST and CLUSTAL W (DNA Data Bank of Japan (DDBJ) homepage).

The bacterial strain of the present invention was determined to be a microbe belonging to the genus *Microbulbifer* based on the result of the analysis of the 16S rRNA sequence. Although it is very likely that this microbe is a microbe belonging to the genus *Microbulbifer* considering the aforementioned microbiological properties, it cannot be completely denied that it can possibly be a microbe of another genus.

Therefore, the present inventors considered that the aforementioned microbial is a new species of the *Microbulbifer* genus based on the result of the 16S rRNA analysis, and named this as *Microbulbifer* sp. 6532A. On Oct. 26, 2006, the present inventors deposited this as 6532A (International Deposit accession number FERM BP-10930, which was transferred from Domestic Deposit accession number FERM P-21069) on the International Patent Organism Depositary of National Institute Of Advanced Industrial Science And Technology (AIST Tsukuba Central 6, 1-1, Higashi 1-chome Tsukuba-shi, Ibaraki-ken 305-8566 Japan).

(Measurement of the Seaweed Decomposition Ability of the Bacterial Strain)

Figure 2:
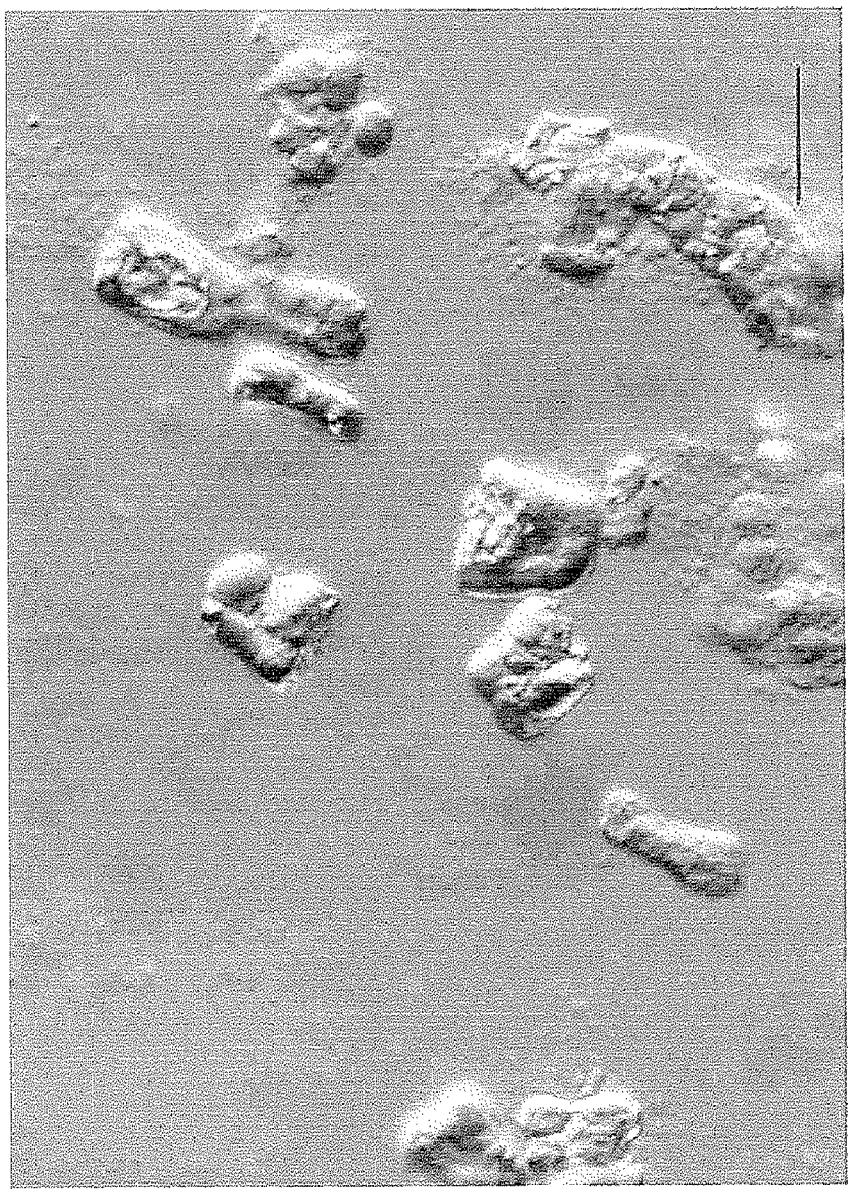
FIG. 2 is a photomicrograph of *Undaria* particles in a single-cell state obtained by degradation of *Microbulbifer* sp. 6532A.

In order to test the seaweed degradation ability of the bacterial strain of the present invention, this microbe was inoculated in an artificial seawater medium (NaCl 30.0 g, KCl 0.7 g, $MgCl_2 \cdot 6H_2O$ 10.8 g, $MgSO4 \cdot 7H_2O$ 5.4 g, $CaCl_2 \cdot 2H_2O$ 1.0 g, $NH_4NO_3$ 1.0 g, $K_2HPO_4$ 0.02 g, Yeast Extract 0.5 g/distilled water 1,000 ml) added with 2% weight of *Undaria* thallus having an average size of about 9.0-15.0 mm squares, and this was cultured at 30° C. with stirring. The result is shown in FIG. 1. In each photographs of FIG. 1, the right test tube indicates the result of a non-inoculated control, and the left test tube indicates the result of a strain 6532A inoculation. When the strain 6532A was inoculated, fragmentation of the seaweed thallus occurred from the third day of culturing, and on the fifth day, a considerable formation of seaweed particles was observed. These seaweed particles were in a single-cell state with each cells separated, and had a property to be suspended uniformly in a culture solution. Furthermore, because these seaweed particles are fine, seaweed particles had a property of being hard to sediment. The seaweed particles obtained by the action of the microbe of the present invention was tested, and it was found that this seaweed particles are about 8 μm single-cell particles (FIG. 2).

*Alteromonas* sp. strain AR06 (FERM BP-5024) and *Alteromonas* sp. strain (FERM P-12346) which are the subject matter of a patent application directed to seaweed degrading bacteria, as well as *Pseudoalteromonas elyakovii* (IAM14594T) and *Pseudoalteromonas espejiana* (IAM12640T), which are causative microbes of Spot-Wounded Frond, and the like are known. A comparative test was carried out for the degradation of the seaweed thallus by the microbe of the present invention and these microbes.

Figure 3:
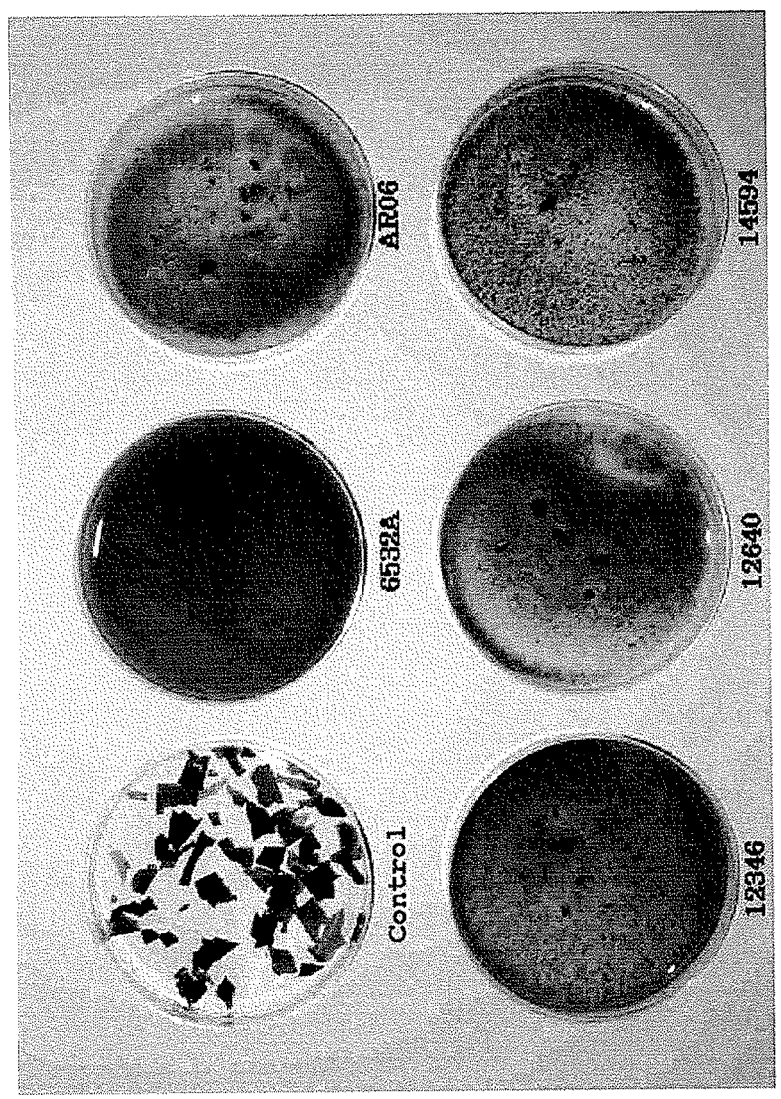
FIG. 3 is a photograph of degraded *Undaria* after cultivation for two days at 30° C. in an artificial seawater medium added with 1% of *Undaria* thallus by stirring. Each strain name of the microbes used is shown below the Petri dishes, respectively. The upper left plate is a control Petri dish.
Figure 4:
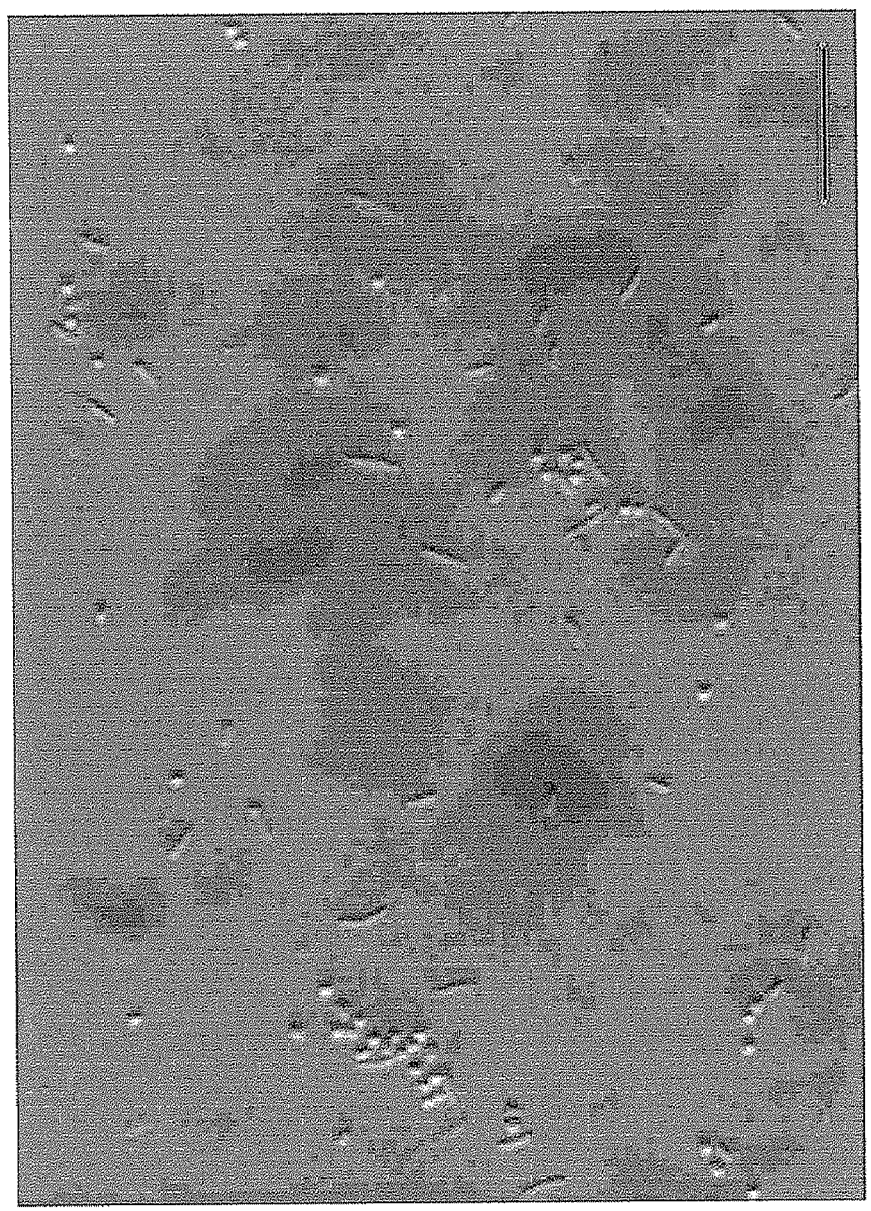
FIG. 4 is a photomicrograph of *Microbulbifer* sp. 6532A.

Each microbe was inoculated into an artificial seawater medium with *Undaria* thallus added (*Undaria* pieces of about 9.0-15.0 mm square), and cultured at 30° C. for two days with stirring. Fragmentation and formation of particles from the seaweed during the cultivation were tested. As a result, the *Undaria* degradation ability of the microbe of the present invention was significantly stronger than those of the other microbes. The comparative results of the seaweed degradation ability among the strain 6532A of the present invention and the four seaweed degradation bacteria are shown in FIG. 3.

(Seaweeds as Raw Materials)

In order to confirm the seaweed that can be used as a raw material, a degradation ability test was carried out for five seaweeds: *Undaria*, kelp, *Ecklonia cava*, *Sargassum horneri* and *Nemacystus decipiens*. Each seaweed thallus was added to the artificial seawater medium to be 1%, and sterilized in autoclave. The strain 6532A was inoculated into the seaweed added artificial seawater medium, and cultured at 30° C. for 14 days with stirring. As a result, formation of seaweed particle from thallus of *Undaria*, kelp, and *Ecklonia cava* in single-cell was observed. On the other hand, no degradation of the thallus was observed for *Sargassum horneri* or *Nemacystus decipiens*.

(Presence or Absence of a Degradation Enzyme for Seaweed Polysaccharides from the Bacterial Strain)

Whether or not the bacterial strain of the present invention has a degradation enzyme for seaweed polysaccharides was tested. At first, strain 6532A was inoculated into the artificial seawater medium added with 2% w/v *Undaria* thallus powder, and cultured for five days, and then, the supernatant thereof was used as a crude enzyme solution. For each polysaccharide of sodium alginate (Katayama chemical industry Co., Ltd., Osaka Japan; viscosity: 500 cps), fucoidan (Sigma) and laminarin (Sigma MO), a 0.5% solution (0.1M phosphate buffer; pH 7.0) was prepared, which is termed as a substrate solution. The substrate solution and the crude enzyme solution were mixed at a ratio of 3:1, and allowed to react at 30° C. for one hour. Then, the increased amount of reduced sugar was measured by Somogyi-Nelson method. As a result, the degrading activity to alginic acid was confirmed.

(Mycological Properties of the Bacterium of the Present Invention)

For the seaweed degrading bacteria obtained in the present method, an enzymatic degradation activity to various kinds of seaweed polysaccharides, i.e., alginic acid, fucoidan and laminarin was measured. The enzyme activity was measured by reacting a bacterial culture supernatant to each seaweed polysaccharide and measuring the increased amount of reduced sugar.

Then, each of the obtained seaweed degrading bacteria was inoculated into the artificial seawater medium added with 1% seaweed thallus (about 9.0-15.0 mm square), and tested for the action on the seaweed thallus. This was cultured at 30° C. for 2-14 days with stirring, and the microbe which showed the degradation and the particles formation from the seaweed thallus were selected.

From this screening, three strains of seaweed degrading microbes having the ability to degrade seaweed and to make seaweed into particles were obtained. Particle formation from the seaweed by these microbes was compared with those by *Alteromonas* sp. strain AR06 (FERM BP-5024) and *Alteromonas* sp. strain (FERM P-12346) which were the subject matter of the patent application for seaweed degradation bacteria [the patent title: a method for production of a brown algae degraded product, Japanese Patent No. 3,079,183], as well as microbes which are causative microbes of Spot-Wounded Frond, including *Pseudoalteromonas elyakovii* (IAM 14594T) and *Pseudoalteromonas espejiana* (IAM 12640T).

As a result of the test, it was found that degradation and particles formation from *Undaria* and kelp by the microbe of the present invention provided finer, more homogenous and superior seaweed particles in suspension and floating properties, compared with that of particles by conventional microbes such as AR06. A microbe that seemed to be especially strong in the ability of particles formation from seaweeds was designated as strain 6532A.

The marine bacteria used for the present invention provided by the aforementioned screening were gram negative, rod-shape bacteria, of O-type as determined by the OF test, and oxidase positive. The results of the bacterial property tests are shown below in table 1.

(1. Morphological Property)
Shape of the cell: Rod
Size of the cell: About 1.0 μm (width)×about 3.2 μm (length)
Presence or absence of motility: Presence
Presence or absence of spore: Absence.

(2. Culture Properties)
In Marine Agar 2216
Producing no pigment, forming a recess in the center of a colony and the colony has a wavy circumference.
Liquefying an agar plate medium.
In Marine Broth 2216
Proliferating well and forming a floc when cultured at 30° C. for 48 hours.

(3. Physiologic Properties)
Gram stain: Gram negative
Pigmentation: Not produced
Oxidase: Positive
Catalase: Positive
Range of growth: No growth at 4° C., good growth at 30° C., and growth is possible at 50° C.
Behavior toward oxygen: Aerobic
O-F test: O-type (according to an MOF medium which is a Hughloifson medium developed for marine bacteria)
Requirement of NaCl: Not growth with 0-1% NaCl, growth at 2.5-5.0%, i.e., NaCl is required for growth.

(4. Polysaccharide Decomposition Enzyme Activity of the Extra Cellular Enzymes)
Alginic acid: Positive
Fucoidan: Negative
Laminarin: Negative
Agar: Positive (strongly: liquefying an agar plate medium in an agar plate).

(5. Measurement of Polysaccharides Decomposing Activity)
The seaweed degrading bacteria was inoculated into the artificial seawater medium added with 2% w/v *Undaria* powder, and cultured for five days, and then the supernatant thereof was obtained as a crude enzyme solution. For each of alginic acid, fucoidan and laminarin, a 0.5% solution (0.1M phosphate buffer; pH 7.0) was prepared, which is a substrate solution. The substrate solution and the crude enzyme solution were mixed at a ratio of 3:1, and allowed to react at 30° C. for one hour. Then, the increased amount of reduced sugar was measured by Somogyi-Nelson method, and the polysaccharides degrading activity was tested as potency of the enzyme activity. As a result, the degrading activity to the alginic acid was confirmed.

(6. Homogeny Searches and Phylogenetic Classification)
The 16S rRNA sequence of the microbe having the aforementioned mycological properties was determined, homogeny search and analysis of taxonomical position was carried out using BLAST and CLUSTAL W (DNA Data Bank of Japan (DDBJ) homepage).

The aforementioned bacterial strain was determined to be a microbe belonging to the genus Microbulbifer based on the result of the analysis of the 16S rRNA sequence. It is very likely that this microbe is a microbe belonging to the genus *Microbulbifer* considering the aforementioned microbiological properties.

Therefore, the present inventors considered that the aforementioned microbial is a new species of *Microbulbifer* genus based on the result of the 16S rRNA analysis, and named this as *Microbulbifer* sp. 6532A. On Oct. 26, 2006, the present inventors deposited this as 6532A (deposit accession number FERM BP-10930, which was transferred from FERM P-21069) on the International Patent Organism Depositary National Institute Of Advanced Industrial Science And Technology (AIST Tsukuba Central 6, 1-1, Higashi 1-chome Tsukuba-shi, Ibaraki-ken 305-8566, Japan).

Typical properties of *Microbulbifer* sp. 6532A are shown in following Table 1.

TABLE 1

| Tested item | Result of the test |
| --- | --- |
| <Morphology> | |
| Medium | Marine Broth |
| Shape of the cell | Rod |
| Size of the cell | 1.0 μm × 3.2 μm |
| Motility | Presence |
| Flagella | Presence |
| Gram stain property | negative |
| Behavior for oxygen | Aerobic |
| Color of colony | white |
| <growth condition> | |
| Optimal temperature | |
| Growth at 4° C. | − |
| Growth at 30° C. | + |
| Growth at 50° C. | + |
| NaCl concentration | |
| 0.0% | − |
| 1.0% | − |
| 2.5% | + |
| 4.0% | + |
| 5.0% | + |
| 7.5% | − |
| 10.0% | − |

TABLE 2

| Tested item | Result of the test |
| --- | --- |
| <Physiological properties> | |
| O—F test | O type |
| Catalase test | + |
| Oxidase test | + |
| Gelatin degrading ability | − |

TABLE 2-continued

| Tested item | Result of the test |
| --- | --- |
| Agar degrading ability | + |
| Esculin degrading ability | + |
| ONPG test | − |
| VP test | − |
| MR test | − |
| Urease productivity | − |
| Hydrogen sulfide productivity | − |
| Utilization of citrate salt | − |
| Indole production | − |
| Nitric acid reducing ability | |
| Denitration | − |
| Nitrate salt reduction | − |
| Assimilation | |
| L-arabinose | − |
| D-xylose | − |
| D-glucose | + |
| D-mannose | + |
| D-fructose | + |
| D-galactose | + |
| Maltose | + |
| Sucrose | − |
| Lactose | − |
| Trehalose | − |
| D-sorbitol | − |
| D-mannitol | − |
| Inositol | − |
| Glycerin | − |
| Starch | + |

(7. Seaweed Decomposition Ability)

In order to test the seaweed degradation ability of the bacterial strain, the microbe was inoculated in the artificial seawater medium added with 2% weight of about 9.0-15.0 mm squares of *Undaria* thallus, and this was cultured at 30° C. with stirring. As a result, fragmentation of the seaweed thallus occurred on the third day in culture, and formation of seaweed particles in a single-cell state was observed on the fifth day in culture (FIG. 1). Testing the resultant seaweed suspension revealed that almost all seaweed particles were separated in a single-cell state, and were homogenously suspended in culture and difficult to sediment due to the fine particles. Testing the resultant seaweed particles obtained by the action of the present microbe revealed that the seaweed particles were about 8 μm single-cell seaweed particles (FIG. 2).

Comparative tests for seaweed thallus degradation were conducted with four strains, which are known as seaweed degrading bacteria, including *Alteromonas* sp. strain AR06 (FERM BP-5024) and *Alteromonas* sp. strain (FERM P-12346), and the bacterium of the present invention. Specifically, each microbe was inoculated to the artificial seawater medium (NaCl 30.0 g, KCl 0.7 g, $MgCl_2.6H_2O$ 10.8 g, $MgSO4.7H_2O$ 5.4 g, $CaCl_2.2H_2O$ 1.0 g, $NH_4NO_3$ 1.0 g, $K_2HPO_4$ 0.02 g, Yeast Extract 0.5 g/distilled water 1,000 ml) added with 1% *Undaria* thallus (*Undaria* pieces in about 9.0-15.0 mm squares). This was cultured at 30° C. for 2 days with stirring. Then, it was tested for fragmentation and particle formation from the seaweed. The results are shown in FIG. 3. In the photograph of FIG. 3, microbe names were respectively shown below the Petri dishes. It was revealed that the *Undaria* degradation effect by the microbe of the present invention was significantly stronger than those of the conventional seaweed degrading bacteria. For example, when using a bacterium of genus *Alteromonas* as used in patent document 1, almost no particle formation from the seaweed occurred, and the seaweed remained as a large mass. This result shows that the present invention is superior to the prior art.

For example, the degradation product produced in Japanese Patent No. 2772772 was obtained by allowing a microbe to act on seaweed powder having a particle size of 44 μm or less and having an average particle of size 23 μm or less. When the bacterial strain 6532A of the present invention was inoculated into the seaweed thallus of about 1 mm squares, the degradation product was obtained. However, when a microbe of Japanese Patent No. 2772772 was used in the same condition, almost no particles was formed from the seaweed powder but in a large mass (as shown in FIG. 3). From these results, the superior effect of the present invention was confirmed.

(8. Seaweeds as Raw Materials)

In order to determine if the seaweed can be used as a raw material, a degradation ability test was carried out for five kinds of seaweeds, *Undaria*, kelp, *Ecklonia cava*, *Sargassum horneri* and *Nemacystus decipiens*. As a result, seaweed particle formation from thallus of *Undaria*, kelp, and *Ecklonia cava* due to single-cell formation was observed. Whereas no degradation of the thallus was observed for *Sargassum horneri* or *Nemacystus decipiens*.

TABLE 3

Ability Of The Microbe To Decompose Various Seaweed

| | Undaria | kelp | Ecklonia cava | Sargassum horneri | Nemacystus decipiens |
| --- | --- | --- | --- | --- | --- |
| 6532A | Yes | Yes | Yes | No | No |

Yes: an ability to degrade seaweed was observed
No: an ability to degrade seaweed was not observed The microbe of the present invention had a strong ability to make seaweeds thallus into a single-cell state, especially *Undaria*, kelp and *Ecklonia cava*. Inoculation of the present bacterial strain with *Undaria*, kelp and *Ecklonia cava* thallus and stir culturing at 30° C. could result in single-cell seaweeds having about 10 mm particle diameter.

(9. Preparation of Seaweed Decomposition Product)

One kg Dry *Undaria* was mixed with 20 L of 3% saline and allowed to swell. This was sterilized at 121° C. for 15 minutes, inoculated with 100 ml culture of the present bacterium, and cultured at 30° C. for five days with stirring to prepare a seaweed degradation product. It should be noted that the culture of the present bacterium was prepared by culturing the present bacterium in a medium having the following composition at 30° C. for 24 hours: dry seaweeds 20.0 g, NaCl 30.0 g, KCl 0.7 g, $MgCl_2.6H_2O$ 10.8 g, $MgSO_4.7H_2O$ 5.4 g, $CaCl_2.2H_2O$ 1.0 g, $NH_4NO_3$ 1.0 g, $K_2HPO_4$ 0.02 g, Yeast Extract 0.5 g; distilled water 1,000 ml).

The prepared seaweed degradation product was spray-dried to obtain 0.95 kg *Undaria* powder. This *Undaria* powder and *Undaria* powder obtained by conventional physical treatments were respectively suspended at a 10% concentration in water, and compared for the texture of the resultant suspensions. As a results, the suspension of the *Undaria* powder of the present invention gave no roughness, and had a smooth taste.

(10. Comparison of the Particle Formation from Seaweeds by Bacterial Degradation)

Japanese Patent No. 2772772 describes that the size of the degradation product produced is 5-10 μm. The present invention is superior compared with this result as shown in the following experiments.

(Materials and Methods)
1) Bacterial Strains
6532A isolated strain (accession number FERM P-21069)
FERM-BP 5024 (strain AR06: National Research Institute of Fisheries Science, Fisheries Research Agency, Japanese Patent No. 2772772)
FERM-P 12346 (*Alteromonas* sp. No. 4778: Maruha Corporation, Japanese Patent No. 3079183)
2) Materials
i) *Undaria* micro powder (Riken Vitamin Co., Ltd., WAKAMIDORI)
ii) *Undaria* thallus (Riken Vitamin Co., Ltd., cut *Undaria* No. 12, *Undaria* pieces: about 1.0 cm square)
3) Methods
i) Each microbe was inoculated with 2% *Undaria* micro powder (or *Undaria* thallus) in the artificial seawater medium. The microbes used for inoculation were previously cultured for 24 hours in a Marine Broth 2216 medium (the composition is shown below) and the culture were adjusted to have an absorbance of 0.1, and 100 µl of this bacterial solution was added to the artificial seawater medium.
ii) The inoculated artificial seawater medium was cultured for a certain period at 120 rpm, 30° C. with stirring, then 1 ml samples were taken out. These samples are referred to as seaweed composition solutions.
iii) The obtained samples were boiled for 10 minutes and stored at 4° C. until a measurement start.
iv) HORIBA laser diffraction/scattering type particle size distribution Analyzer LA-920 (Measurable grain size range: 0.1-2000 µm) was used as an analyzer.

Figure 5:
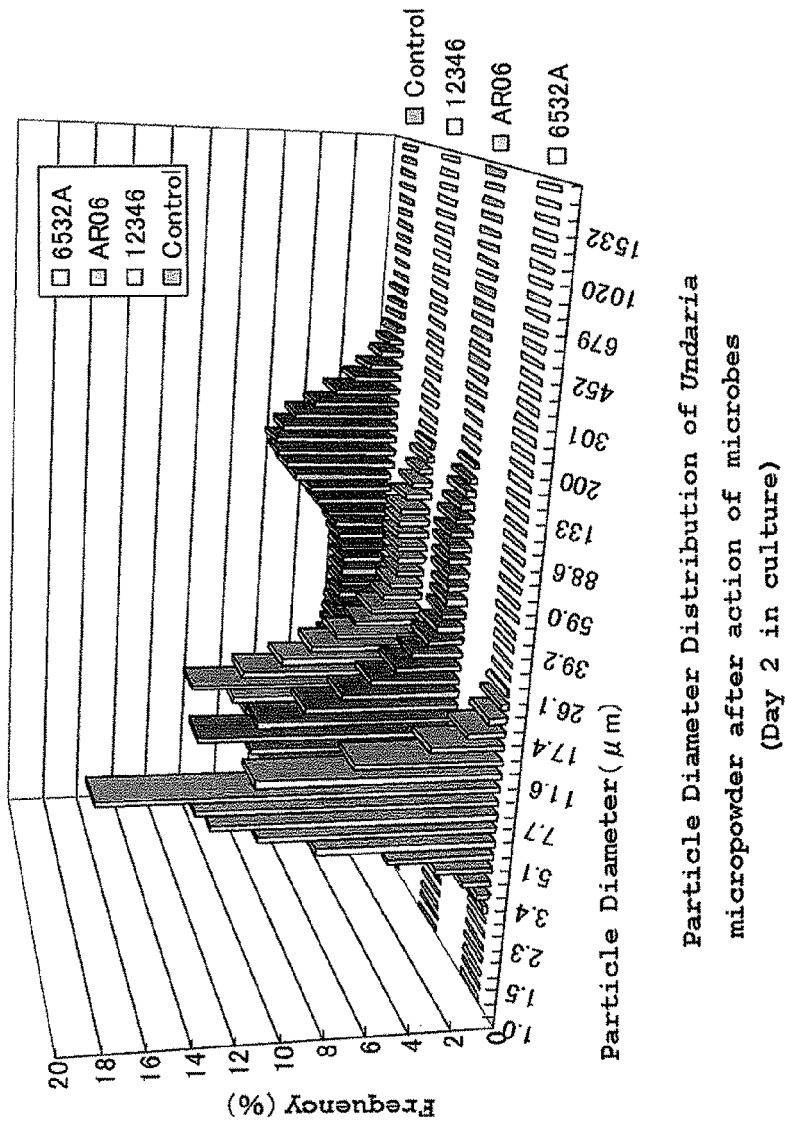
FIG. 5 shows the particle diameter distributions of post-treatment *Undaria pinnatifida* micro powder obtained by microbial treatment. Particle diameter distributions of post-treatment *Undaria pinnatifida* micro powder obtained after a microbe strain 6532A, strain AR06 or strain 12346 was inoculated into a medium containing pre-treatment *Undaria pinnatifida* micro powder and cultured for two days are shown.
Figure 6:
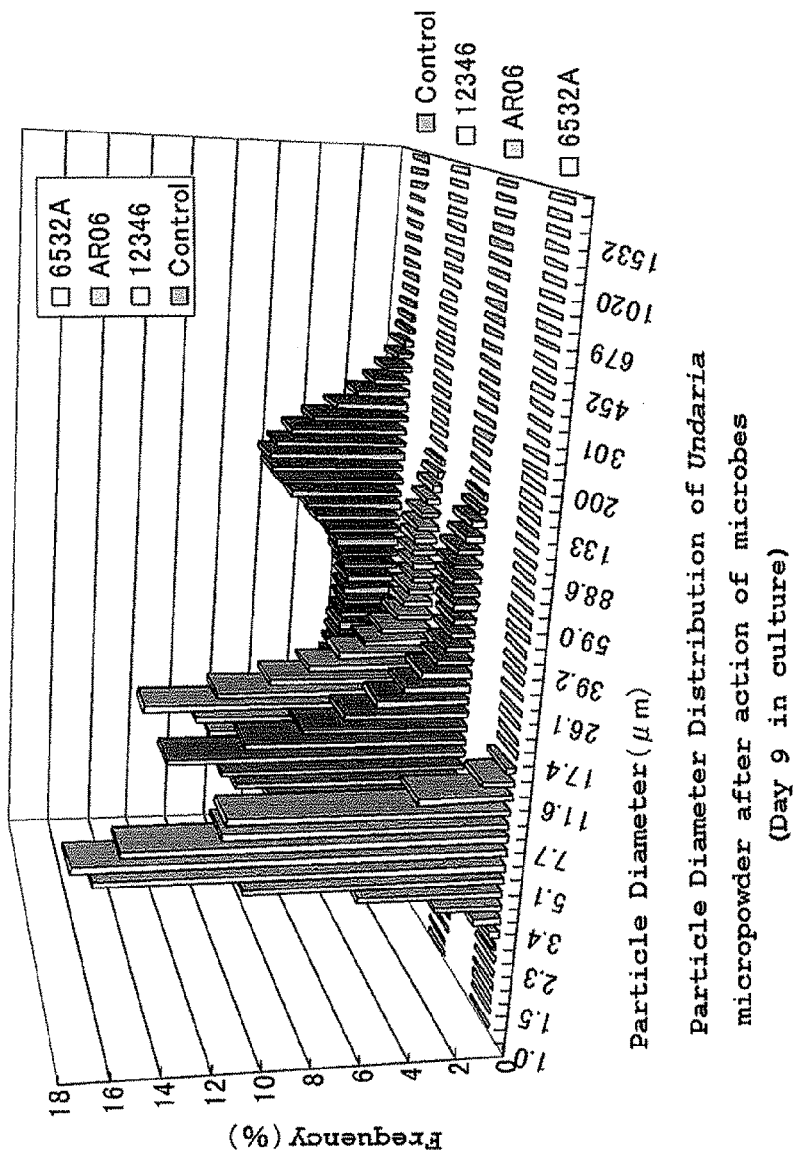
FIG. 6 shows the particle diameter distributions of post-treatment *Undaria* micro powder obtained by microbial treatment. Particle diameter distributions of post-treatment *Undaria* micro powder obtained after a microbe strain 6532A, strain AR06 or strain 12346 was inoculated into a medium containing pre-treatment *Undaria* micro powder and cultured for nine days are shown.
Figure 7:
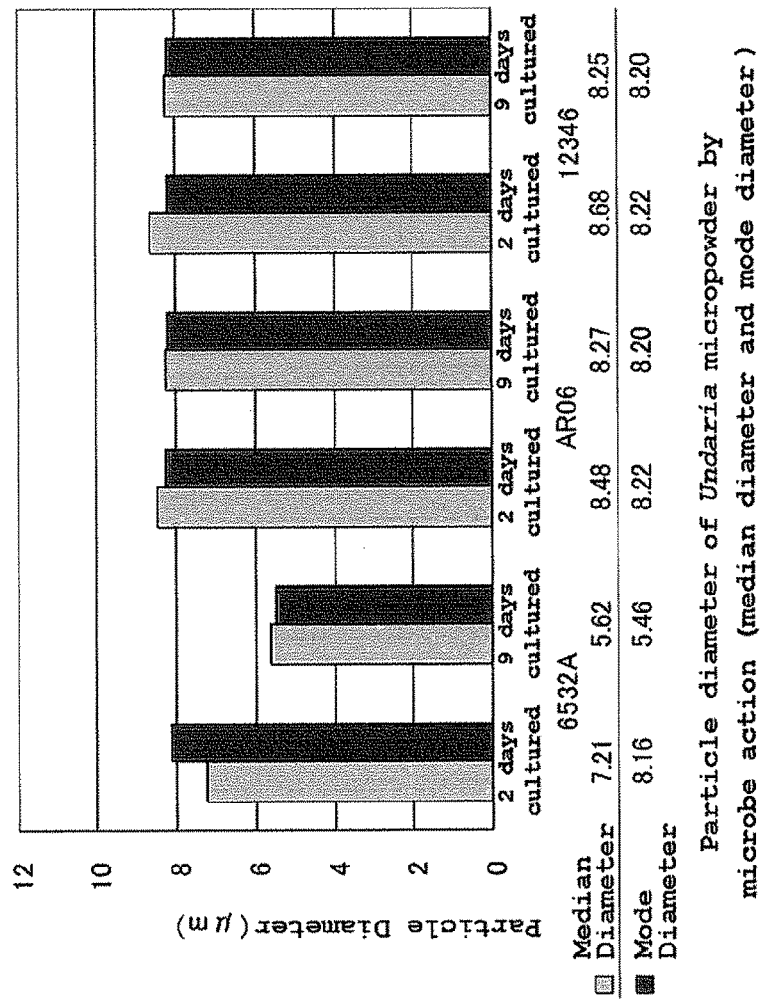
FIG. 7 shows the particle diameter (median diameter and mode diameter, unit in μm) of post-treatment *Undaria* micro powder obtained by microbial treatment. The average particle diameters of post-treatment *Undaria* micro powder after a microbe strain 6532A, strain AR06 or strain 12346 was inoculated into a medium containing pre-treatment *Undaria* micro powder and cultured for two or nine days are shown.
Figure 8:
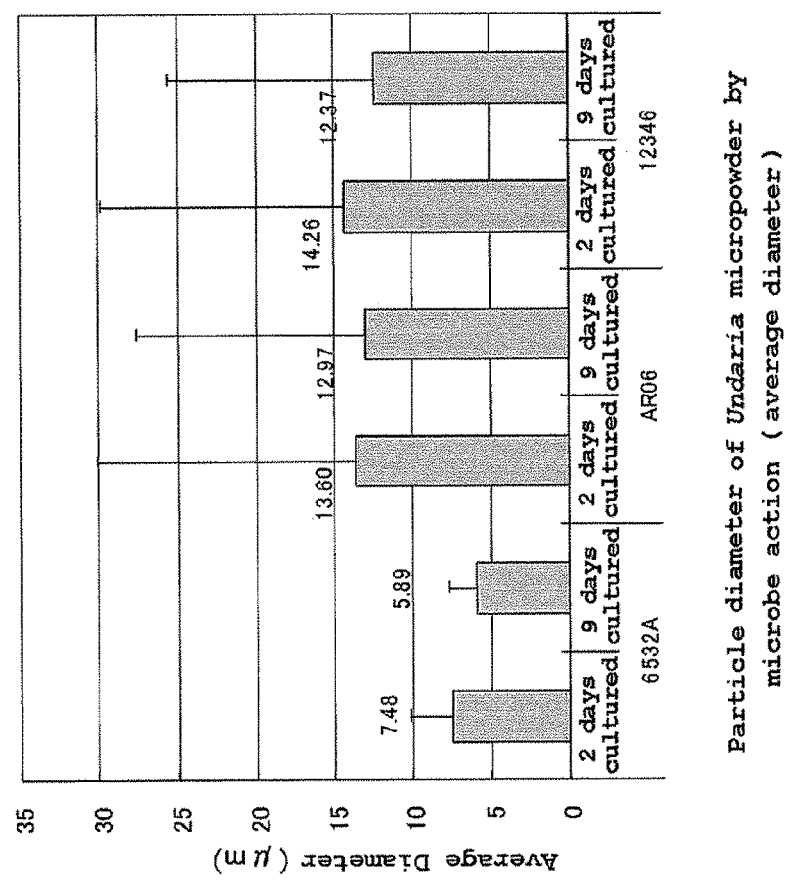
FIG. 8 shows the average particle diameter of post-treatment *Undaria* micro powder obtained by microbial treatment. The average particle diameters of post-treatment *Undaria* micro powder after a microbe strain 6532A, strain AR06 or strain 12346 was inoculated into a medium containing pre-treatment *Undaria* micro powder and cultured for two or nine days are shown.

(Results and Discussion)
1) Effects on *Undaria* Micro Powder
According to the results of FIGS. 5, 6 and 7, it was found that 6532A produced the finest seaweed micro powder. Furthermore, FIG. 8 shows the average diameter and the standard deviation of the particles. Comparing to other microbes, 6532A provided a smaller average diameter of the particles and a much smaller standard deviation. Thus, it is concluded that using the bacterial strain of the present invention, seaweed degradation products with small deviation and uniform particles were generated.

Figure 9:
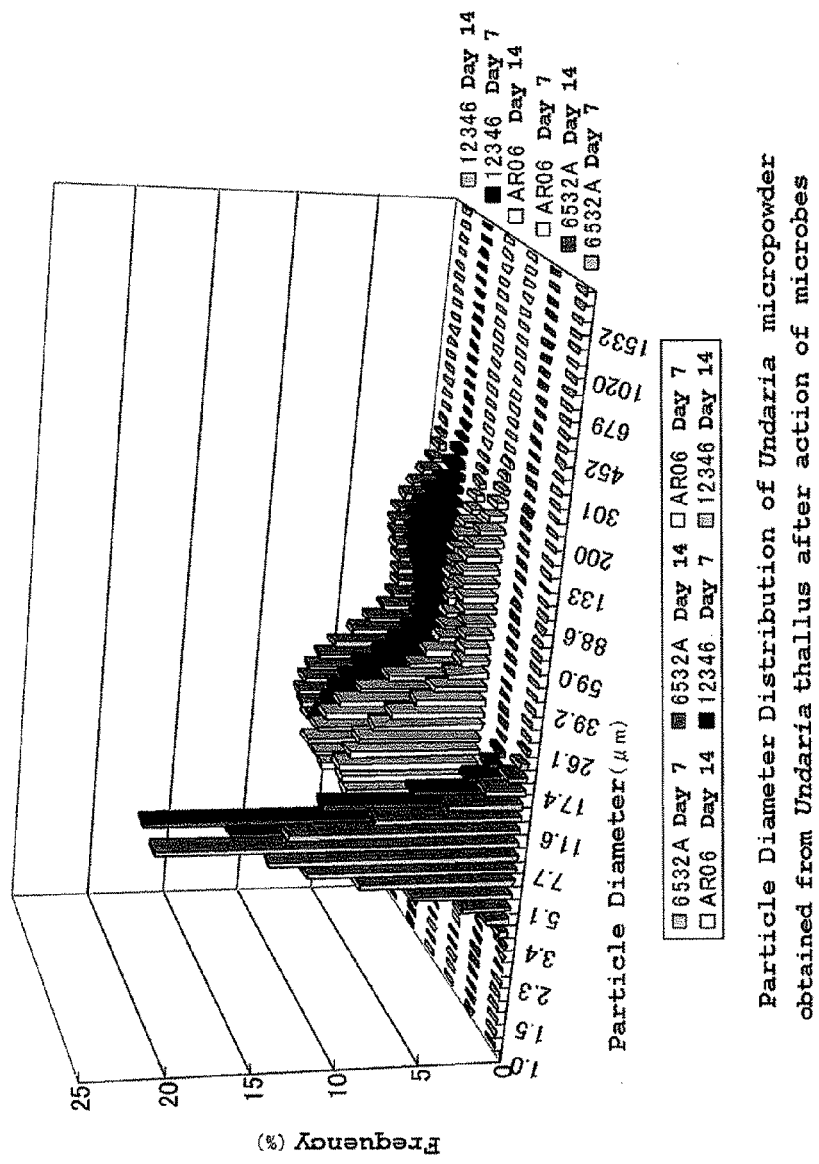
FIG. 9 shows the particle diameter distributions of *Undaria* micro powder obtained after *Undaria* thallus (about 10 mm square) was treated by the microbe for seven days or 14 days. The particle diameter distributions of *Undaria* micro powder after a microbe strain 6532A, strain AR06 or strain 12346 was inoculated into a medium containing *Undaria* thallus and cultured for seven or 14 days are shown.

2) Effects on *Undaria* thallus
The results of FIGS. 9-11 revealed that degradation of seaweed thallus by 6532A was much stronger than that of other bacteria, and that enough particle formation was processed in about 1 week. In the case of strain AR06 or strain 12346, even if the culture period was extended longer, the particle formation from the seaweeds was hardly processed. From these results, strain 6532A clearly has a higher ability to degrade seaweed thallus than other strains.

3) Summary
These results indicate that strain 6532A has high ability to form seaweed particle, and can produce uniform degradation products with smaller deviation, compared with the conventionally known bacterial strains.

TABLE 4

| Marine Broth Medium (in 100 ml) | |
|---|---:|
| Peptone | 5 g |
| Yeast Extract | 1 g |
| Ferric Citrate | 0.1 g |
| Sodium chloride | 19.45 g |
| Magnesium Chloride | 5.9 g |
| Magnesium Sulfate | 3.24 g |
| Calcium Chloride | 1.8 g |
| Potassium Chloride | 0.55 g |
| Sodium Bicarbonate | 0.16 g |
| Potassium Bromide | 0.08 g |
| Strontium Chloride | 34 mg |
| Boric Acid | 22 mg |
| Sodium Silicate | 4 mg |
| Sodium Fluoride | 2.4 mg |
| Ammonium Nitrate | 1.6 mg |
| Sodium Phosphate | 8 mg |

The present invention was illustrated using the preferred embodiment of the present invention as above, but the present invention should not be interpreted as limited to these embodiments. It is to be understood that the range of the present invention should be interpreted only by claims. Those skilled in the art would appreciate from the description of the specific preferred embodiments of the present invention, that equivalent range can be carried out based on the description of the present invention and the common technical knowledge. It is to be understood that the patents, patent applications and references cited in the present specification are incorporated in reference as if the contents itself is specifically described in the present specification.

INDUSTRIAL APPLICABILITY

In accordance with the present invention, a method to prepare almost single-cell state and almost uniform seaweed degradation products comprising a certain marine bacteria to act on seaweeds. Compositions for preparing such seaweed degradation products are also provided. In accordance with the present invention, food and beverage products containing such seaweed degradation products are also provided.

The invention claimed is:

1. A method to prepare a uniform seaweed degradation product having good suspension property comprising contacting a bacterium having an endogenous 16S rRNA sequence consisting of the nucleic acid sequence as recited in SEQ ID NO: 1 with a seaweed, wherein said bacterium is *Microbulbifer* sp, strain 6532A (accession number FERM P-21069).

2. The method according to claim 1, wherein said bacterium has the following mycological properties:
   A) Morphological properties in an artificial seawater medium:
      i) Shape of the cell: Rod
      ii) Size of the cell: About 1.0 μm (width)×about 3.2 μm (length)
      iii) Presence or absence of motility: Presence
      iv) Presence or absence of spore: Absence;
   B) Culture properties:
      i) In Marine Agar 2216:
         a) Producing no pigment, forming a recess in the center of a colony and the colony having a wavy circumference;
         b) Liquefying an agar plate medium;
      ii) In Marine Broth 2216:
         a) Proliferating well and forming a floc when cultured at 30° C. for 48 hours;
   C) Physiologic Properties:
      i) Gram stain: Gram negative
      ii) Pigmentation: Not produced
      iii) Oxidase: Positive
      iv) Catalase: Positive
      v) Range of growth: No growth at 4° C., good growth at 30° C., and growth is possible at 50° C.
      vi) Behavior toward oxygen: Aerobic
      vii) O-F test: O-type
      viii) Requirement of NaCl: No growth with 0-1% NaCl, growth at 2.5-5.0% NaCl, NaCl is required for growth;
   D) Polysaccharide Decomposition Activity Of The Extracellular Enzymes:
      i) Alginic acid: Positive
      ii) Fucoidan: Negative
      iii) Laminarin: Negative
      iv) Agar: Positive.

3. The method according to claim 1, wherein said seaweed is a brown algae.

4. The method according to claim 1, wherein said seaweed is *Undaria*, kelp or *Ecklonia cava*.

5. A method to prepare a uniform seaweed degradation product having good suspension property comprising contacting a crude enzyme solution with a seaweed, wherein the crude enzyme solution is prepared from a bacterium having an endogenous 16S rRNA sequence consisting of the nucleic acid sequence as recited in SEQ ID NO: 1, and wherein said bacterium is *Microbulbifer* sp, strain 6532A (accession number FERM P-21069).

6. The method according to claim 5 wherein said seaweed is a brown algae.

* * * * *